(12) United States Patent
Podhorna et al.

(10) Patent No.: US 12,059,408 B2
(45) Date of Patent: Aug. 13, 2024

(54) TREATMENT OF COGNITIVE IMPAIRMENT ASSOCIATED WITH SCHIZOPHRENIA

(71) Applicant: Boehringer Ingelheim International GmbH, Ingelheim am Rhein (DE)

(72) Inventors: Jana Podhorna, Wiesbaden (DE); Holger Rosenbrock, Mittelbiberach (DE); Sun Young Yum, Seoul (KR); Yihua Zhao, Bedford, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/399,094

(22) Filed: Aug. 11, 2021

(65) Prior Publication Data

US 2022/0047562 A1    Feb. 17, 2022

(30) Foreign Application Priority Data

Aug. 13, 2020   (EP) ..................... 20190925

(51) Int. Cl.
  *A61K 31/422*  (2006.01)
  *A61P 25/18*   (2006.01)
  *A61P 25/28*   (2006.01)

(52) U.S. Cl.
  CPC ............ *A61K 31/422* (2013.01); *A61P 25/18* (2018.01); *A61P 25/28* (2018.01)

(58) Field of Classification Search
  CPC ......... A61K 31/422; A61P 25/28; A61P 25/18
  See application file for complete search history.

(56) References Cited

U.S. PATENT DOCUMENTS

| | | | |
|---|---|---|---|
| 6,673,799 B1 | 1/2004 | Taniguchi | |
| 7,220,744 B2 | 5/2007 | Jolidon et al. | |
| 7,317,125 B2 | 1/2008 | Bolin et al. | |
| 7,332,495 B2 | 2/2008 | Li et al. | |
| 7,473,787 B2 | 1/2009 | McHardy et al. | |
| 7,557,114 B2 | 7/2009 | Jolidon et al. | |
| 7,951,836 B2 | 2/2011 | Bertani | |
| 8,188,139 B2 | 5/2012 | Jolidon et al. | |
| 8,288,435 B2 | 10/2012 | Aissaoui et al. | |
| 8,497,289 B2 | 7/2013 | Lindsley et al. | |
| 8,816,079 B2 | 8/2014 | Maeda et al. | |
| 2006/0167000 A1 | 7/2006 | Barnham et al. | |
| 2008/0287455 A1 | 11/2008 | Jolidon et al. | |
| 2010/0035914 A1 | 2/2010 | Bertani et al. | |
| 2012/0022099 A1 | 1/2012 | Zlotnikov et al. | |
| 2015/0087673 A1 | 3/2015 | Hitoshi et al. | |

FOREIGN PATENT DOCUMENTS

| | | |
|---|---|---|
| CN | 1381449 A | 11/2002 |
| CN | 107540636 A | 1/2018 |
| EP | 1396487 A1 | 3/2004 |
| EP | 2556829 A1 | 2/2013 |
| JP | 2008239568 A | 10/2008 |
| JP | 2013107881 A | 6/2013 |
| WO | 010078348 A2 | 10/2001 |
| WO | 200208221 A2 | 1/2002 |
| WO | 2004089363 A1 | 10/2004 |
| WO | 2005011653 A2 | 2/2005 |
| WO | 2005037216 A2 | 4/2005 |
| WO | 2006044174 A2 | 4/2006 |
| WO | 2006106425 A1 | 10/2006 |
| WO | 2007053394 A1 | 5/2007 |
| WO | 02009016560 | 2/2009 |
| WO | 2009139576 A2 | 11/2009 |
| WO | 2010080357 A1 | 7/2010 |
| WO | 0210116328 | 10/2010 |
| WO | 10150281 A2 | 12/2010 |
| WO | 2011136292 A1 | 11/2011 |
| WO | 2011143365 A1 | 11/2011 |
| WO | 2012016217 A1 | 2/2012 |
| WO | 2012037349 A2 | 3/2012 |
| WO | 2012158784 A2 | 11/2012 |
| WO | 2013017657 A1 | 2/2013 |
| WO | 2013066714 A1 | 5/2013 |
| WO | 2000171163 | 1/2014 |
| WO | 2014139144 A1 | 9/2014 |
| WO | 2014191336 A1 | 12/2014 |
| WO | 2015048547 A2 | 4/2015 |
| WO | 2015101957 A2 | 7/2015 |
| WO | 2016073774 A2 | 5/2016 |
| WO | 2016138114 A1 | 9/2016 |
| WO | 2016138144 A2 | 9/2016 |
| WO | 2017222930 A1 | 12/2017 |
| WO | 2018159827 A1 | 9/2018 |
| WO | 2018170225 A1 | 9/2018 |
| WO | 2018183145 A1 | 10/2018 |
| WO | 2019046931 A1 | 3/2019 |

(Continued)

OTHER PUBLICATIONS

Abstract in English for WO2009139576 published Nov. 19, 2009.
Alessandri, TRPC1 and TRPC6 Channels Cooperate with TRPV4 to Mediate Mechanical Hyperalgesia and Nociceptor Sensitization, THe jpurnal od Neuroscience, 2009, vol. 29, p. 6217-6228.
Antigny, Transient Receptor Potential Canonical Channel 6 Links, Institut de Psysiologie, vol. 44, 2011.
Baldovini et al., 3-Oxa- and 3-Azabicyclo[3.1.0]hexan-2-ones via Tandem Radical Cydlization-Intramolecular SN2 Reactions, J of Organic Chemistry, 1996, vol. 61, p. 3205-3208.

(Continued)

*Primary Examiner* — Kamal A Saeed
(74) *Attorney, Agent, or Firm* — David L. Kershner

(57) ABSTRACT

The invention relates to the treatment of cognitive impairment associated with schizophrenia (CIAS) with a specific GlyT1 inhibitor ([5-(methylsulfonyl)-2-{[(2R)-1,1,1-trifluoropropan-2-yl]oxy}phenyl]{(1R,5R)-1-[5-(trifluoromethyl)-1,2-oxazol-3-yl]-3-azabicyclo[3.1.0]hex-3-yl}methanone). A 12-week treatment in a phase 2 study showed improvement in cognitive function as measured by the MATRICS Consensus Cognitive Battery (MCCB) overall composite score.

24 Claims, 2 Drawing Sheets

(56) References Cited

FOREIGN PATENT DOCUMENTS

WO          2020223419 A1    11/2020

OTHER PUBLICATIONS

Bergdahl, Plasticity of TRPC expression in arterial smooth muscle, Am J. Physiol vol. 22, 2004.
Chigrupati, Receptor Channel TRPC6 is a key mediator of Notch Driven Glioblastoma Growth and Invasiveness, Tumor and Stem cell Biology, 2009.
Clapham, The TRP Ion channel Family, Nature, 2001.
Clarson, Store Operated CA2 entry in first trimester and term human placenta, J. Psysiol, 2003.
CN103360343 abstract cited herein, 2013.
Davis, A TRPC6-dependent pathway for myofibroblast transdifferentiation and wound healing in vivo, Dev. cell, 2012.
Desai, TRP channels and mice deficient in channels, Eur, J, Physiol, 2005.
Ding, Essential Role of TRPC6 Channels in G2M Phase Transition and Development of Human Glioma, Oxford Univ. Press, 2010.
Ding, Pyrazolo [1,5-a] pyrimidine TRP6 antagonists, Cancer Letters, 2018.
Dutille, High Expression of Trasient Receptor Potential Channels in Human Breast Cancer Epithelial Cells and Tissues, Cell Physiol Biocehem, 2011.
Eckel, TRPC6 Enhances Angiotensin II-induced Albunieria, JASN, 2011.
Finney-Hayward, Expression of Transient Receptor Potential C6 Channels in Human Lung Macrophages, American Journal of Respiratory cell and Molecular Biol, 2010.
Gilligan et al., Divergent mechanisms for the Dealkoxycarbonylation of a 2-(3-Azetidiny)malonate by Chloide and Cyanide, Tetrahedron Letters, 1994, vol. 35, No. 21, pp. 3441-3444.
Hafner, A Larixol Congener with High Affinity and Subtype Selectivity toward TRP6, ChemPubSoc Europe, 2018, vol. 13, p. 1028-1035.
Hofman, Direct Activation of human TRPC6 and TRPC3 channels by diacylglycerol, Letters to Nature, 1999.
International Search Report and Written Opinion for PCT/EP2018/079276 dated Oct. 25, 2018.
International Search Report and Written Opinion for PCT/EP2018079276.
International Search Report and Written Opinion for PCT/EP2019/053525 dated Apr. 10, 2019.
International Search Report, dated May 15, 2019 for PCT/US2019/017939.
International Search Report, PCT/ISA/210, and Written Opinion, form PCT/ISA/237, for corresponding application PCT/EP2012/065140, dated Aug. 27, 2012.
Iyer, Receptor Channel TRPC6 orchestrate the activation of human hepatic stellate cell under hypoxia condition, Experimental Cell Research, 2015.
Johannson, Cebrovascular endothelin I hyperreactivity is associated with transient receptor potential canonical channels 1 and 6 activation and delayed cerebral hypoperfusion after forebrain iscachemia in rats, Acta Pysiol, 2015.
Krall, Podocyte-Specific Overexpression of Wild-Type or Mutalnt TRPC6 in Mice, PLOS One, 2010.
Ku, Expression of Transient ReceptorChannel Proteins, J. Soc Gynol Testing, 2006.
Kunichika, Bosentan Inhibiits Transient Receptor Potential Channel Expression in Pulmonary Vascular Myocytes, Amer. J. of Respiratory and Critical Care Medicine, 2004.
Kuwahara, TRPC6 fulfills a calcineurin signalling circuit during pathologic cardiac remodelling, Journal of Clincal Investigation, 2006.
Lei, The role of mechanical tension on lipid raft dependent PDGF-induced TRPC6 activation, Biomaterials, 2014.

Mayer, Discovery and Pharmacological characterization of a novel potent inhibitor, British Jour. of Phamra, 2015.
Medda et al., 3,4-Methano-β-Proline: A Conformationally Constrained β3-Amino Acid, Synlett, vol. 2009, No. 06, p. 921-924.
Moller, Induction of TRPC6 Channel in Acquired Forms of Proteneuric Kidney Disease, J. Am. Socio Nephrol. 2007.
Motoyama, Discovery of a bicyclo [4.3.0] nonane DS88790512 as a potent, selective, and orally bioavailable blovker of transient receptor potential canonical 6, Bioorganic & Medicinal Chem letters, 2018, p. 2222-2227.
Quiros, Identifcation of TRPC6 as a possible candidate target gene within an amplicon at 11q21-q22.2 for migratory capacity in head and neck squamos cell carcinomas, BMC cancer, 2013.
Reiser, TRPC6 is a glomerular slit diaphragm-associated channel required for normal renal function, Nature genetics, 2005.
Rosenbaum, Hypercholesterolemia inhibits re-endotheliaization of arterial injuries by TRPC channel activation, Journal of Vascular Surgery, 2014.
Sadowski, A single gene cause in 29.5 of cases of steroid resistant nephrotic syndrome, JASN, 2014.
Schlondorff, TRPC6 mutations associated with focal segmental glomerulosclerosis cause constitutive actication of NFAT-dependent transciptioin, Am. J. Cell Physiol. 2009.
Seo, Combined TRPC3 and TRPC6 blockade by selective small-molecule or genetic deletion inhibits pathological cardiac myopathy, PNAS, 2013.
Sharma, Review of Transient Receptor Potential Canonical Channel Modulators, Jour. of Medicinal Chem, 2019.
Song, Critical Role of TRPC6 channels in the development of Human renal cell carcinoma, Mol. Biol Rep, 2013.
Tauseef, TLR4 activation of TRPC6-dependent calcium dignaling mediates endotoxin-induced lung vascular permeability, J. of Experimental Med, 2009.
Thilo, Pulsatile Atheroprone Shear Stress Affects the Expression of Transient Receptor Potential Channels in Human Endothelial Cells, Dept. of Nephrology, 2012.
Thilo, VEGF regulates TRPC6 channels in podocytes, Nephrol Dial Transplant, 2012.
Urban, Identificationand Validation of Larixyl Acetate as a potent TRPC6 inhibitor, Molecular Pharma, 2015.
Wang, Effects of chronic ecposure to cigarette smoke on canonical transient receptor potential expression in rat pulmonary arterial smooth muscle, Am. J. Cell Physiol 2013.
Washburn, The discovery of potent blovkers of the canonical transient receptor Channels, Bioorganic & Medicinal Chem. Letters, 2013, p. 4979-4984.
Weissman, Activation of TRPC6 channels is essential for lung ischamia-reperfusion induced oedema in mice, Nature Communications, 2011.
Wen, Regulation of Multi-drug Resistance in hepato cellular carcinoma cells is TRPC6/Calcium delendent, Nature, 2015.
Winn, A mutation in the TRPC6 Cation Channel causes Familial focal Segmental Glomerulosclerisi, Sciene Mag.org, vol. 38, 2005.
Written Opinion for PCT/US2019/017939 dated May 15, 2019.
Wu, TRPC channels are necessary mediators of patholgic cardic hypertropy, PNAS, 2010.
Xie, Cardioprotection by Klotho through downregulation of TRPC6 channels, Nature Communincations, 2012.
Xie, Soluble Kloto protects against Uremic cradiomyopahy independently of Fibroblast growth Factor 23 and Phophate, JASN, 2015.
Yu, Enhanced expression of transient receptor potential channels of idiopathic pulmonary arterial hypertension, PNAS, 2004.
Zhang, High expression of transient potential rceptor C6 correclated with poor prgonosis in pateients with esophageal squamous cell carcinmoa, Med. oncol, 2013.
Zhang, Micro-RNA-26a prevents endotherial cell apoptosis by directly targeting TRPC6 in the setting of atherosclerosis, Nature, 2015.
Holz, Investigational Treatment for Cognitive Impairment Associated with Schizophrenia receives FDA Breakthrough therapy designation, Press Release, BI, from May 24, 2021.

(56) References Cited

OTHER PUBLICATIONS

Moschetti, Safety, Tolerability, and Pharmacokinetics of Oral BI 425809, a-Glycine Transporter 1 Inhibitor, in Healthy male volunteers: Eur. J. Drug Metab Pharmacokinet. Vol. 43, 2018, p. 239-249.

Clinical Trials, NCT02832037, Clinical Trial of BI425809 Effect on Cognition and Functional Capacity in Schizophrenia, A phase II Randomised, Double Blind, Placebo controlled Parallel group trial, May 20, 2020, 6 pages.

Rosenbrock, Evaluation of Pharmacokinetics and Pharmacodynamics of BI 425809, Clin. Trasl Sci., vol. 11, 2018, p. 616-623.

Toader, Schitz Bulletin, Effects of Metabotropic Glutamate, 2019 Abstracts, 2 pages.

Moschetti, Safety, Tolerability and Pharmacokinetics of Oral BI 425809, Eur. J. Drug Pharmcokinetics, vol. 43, 2018, 11 pages.

TREATMENT OF COGNITIVE IMPAIRMENT ASSOCIATED WITH SCHIZOPHRENIA

FIELD OF THE INVENTION

The present invention relates to a specific compound, which a GlyT1 inhibitor, and its use for the treatment of Schizophrenia and cognitive impairment associated with schizophrenia (CIAS).

BACKGROUND OF THE INVENTION

Schizophrenia is a chronic devastating disorder, starting early in life and imposing a large health care burden in terms of hospitalisation, chronic treatment, and lost productivity, with treatment and care for schizophrenia patients accounting for between 1.5% and 3% of the total national health expense in the most developed countries [Altamura C, Galderisi P, Rocca A, et al. *Ital J Psychopathol* 2014; 20:223-43], [Knapp M, Mangalore R, Simon J. *Schizophr Bull* 2004; 30:279-93].

The global and societal burden of schizophrenia is large with the World Health Organization ranking it as the 12$^{th}$ most disabling disorder worldwide. Patients with schizophrenia have significantly lower life expectancy, and with suicide accounting for approximately 15% of deaths, the suicide rate is 5-fold higher in this patient population. Individuals with this disorder also experience high rates of co-morbid illnesses such as heart disease, stroke, diabetes and respiratory diseases [Charlson F J, Ferrari A J, Santomauro D F et al. *Schizophr Bull* 2018; 44(6): 1195-1203].

The economic burden of schizophrenia is enormous. Annual costs associated with schizophrenia in the United States have been estimated to be more than 150 billion USD [Cloutier M, Aigbogun M S, Guerin A, et al. *J Clin Psychiatry.* 2016; 77(6):764-771]. Lifetime prevalence of schizophrenia has been stable over decades at approximately 1%. It is estimated that nearly 21 million people are living with schizophrenia worldwide. The onset of schizophrenia is typically during late adolescence or early adulthood with males showing peak onset between 21 and 25 years old and women displaying two peaks in onset, between 25 and 30 years old and after 45 years old.

Schizophrenia represents as a heterogeneous clinical syndrome. Individuals have many symptoms at the same time. The symptoms may be divided into three broad categories [McClellan J, Stock S, *J Am Acad Child Adolesc Psychiatry* 2013; 52(9); 976-990], [Mueser K T, McGurk S R. Lancet 2004; 363; 2063-2072]:

Positive symptoms—such as hallucinations, delusions, thought disorders, and movement disorders
Negative symptoms—such as flat affect, anhedonia, lack of ability to begin and sustain planned activities
Cognitive symptoms—such as poor executive functioning, trouble focusing or paying attention, and impairment of working memory and verbal and visual learning and memory. Cognitive symptoms present early in the course of the disease.

Schizophrenia is characterised by episodes of acute exacerbation when symptoms are particularly severe, and episodes of relative stability with predominant negative and cognitive impairment called residual phase. Fluctuation between acute episodes and residual phases is characteristic for schizophrenia, however the length of residual phases varies significantly and changes over the course of the disease.

Cognitive impairment, a core feature of schizophrenia [Frangou S. *Child Psychiatr Clin* 2013; 22(4); 715-726], has been shown to be a major determinant of poor functional outcome [Green M F. *Am J Psychiatry* 1996; 153(3); 321-330], [Green M F, Kern R S, Braff D L, Mintz J. *Schizophr Bull* 2000; 26(1); 119-136]. Patients with schizophrenia perform significantly worse (about 1-2 standard deviations lower) than controls on almost all neuropsychological tests [Keefe R S E, Fox K H, Harvey P D, Cucchiaro J, Siu C, Loebel A. *Schizophr Res* 2011; 125(2/3); 161-168], [Heinrichs R W. *Am Psychol* 2005; 60(3); 229-242]. While many neuropsychiatric disorders are associated with some degree of cognitive dysfunction, the impairments seen in schizophrenia tend to be more severe and more independent of the grade of severity of other symptoms.

Neurocognitive deficits can be detected early in the course of disease. Already at first episode of psychosis, neurocognitive testing identifies an impairment of about 1 standard deviation (SD) below the norm, which is largely unrelated to positive symptoms. Cognitive deficits appear to be relatively stable over the first years of psychotic illness and affect same cognitive domains as in adults with stable schizophrenia [Barder H E, Sundet K, Rund B R, et al. *Schizophr Res* 2013; 149; 63-69.-1771].

Cognitive deficits can be considered as indicators of a poor prognosis of psychosis as poor neurocognitive performance in these patients is associated with poor psychosocial functioning, especially in the areas of interpersonal functioning and educational/vocational performance. In patient interviews on the burden of schizophrenia, patients reported most burdensome symptoms to be related to cognition and functional difficulties such as poor memory, difficulty communicating, poor attention, feeling mentally blocked and forgetting names or things in conversations.

Clinical studies testing compounds on cognition require clinically stable patients for inclusion and as such, primarily recruit patients in their 30's and 40's. Given they are affected by the disorder for a decade or longer, many patients suffer from overt functional impairment.

Schizophrenia is managed with pharmacological and psychosocial treatments.

Antipsychotics are the primary medication for schizophrenia, with major effects on the reduction of 'psychotic' symptoms and prevention of relapses (maintenance) but demonstrate virtually no beneficial effects on cognition in schizophrenia [Nielsen R E, Levander S, Telleus G K, Jensen S O W, Christensen T O, Leucht S. *Acta Psychiatr Scand* 2015; 131; 185-196].

Accessible and effective treatment of cognitive impairment associated with schizophrenia (CIAS) remains a highly unmet medical need. To date, there is no approved pharmacological treatment for CIAS. Compound I represents a new potential treatment for this serious condition and could lead to improved outcomes and better quality of life. Based on the high unmet need to treat cognitive deficits, the US Food and Drug Administration (FDA) and the National Institute of Mental Health (NIMH) have collaboratively developed guidelines for CIAS therapy development through the MATRICS (Measurement And Treatment Research to Improve Cognition in Schizophrenia) initiative [Buchanan R W, Davis M, Goff D, et al. *Schizophr Bull* 2005; 31(1); 5-19.], [Buchanan R W, Keefe R S E, Umbricht D, Green M F, Laughren T, Marder S R. *Schizophr Bull* 2011; 37(6); 1209-1217]. The requirements of these guidelines are also reflected in the European Medicines Agency (EMA) *Guideline on clinical investigation of medicinal products, includ-* ing depot preparations in the treatment of schizophrenia (EMA/CHMP/40072/2010 Rev. 1).

Compounds for treatment of cognitive impairment should be tested during stable phase per MATRICS recommendations and EMA guidance while efficacy of compounds for treatment of psychosis (e.g. antipsychotics) is primarily assessed during the acute/psychotic phase. Indeed, the average age of patients participating in adult studies in CIAS and negative symptoms is about 40 years and older.

The mean cognitive impairment in patients with schizophrenia is severe, approximately 1-2 SD below the mean of healthy controls, even though the distributions have substantial overlap [Keefe R S. *J Clin Psychiatry* 2014; 75(Suppl 2); 8-13]. It is believed that all patients with schizophrenia exhibit some degree of cognitive impairment compared to their premorbid level. Therefore, the NIMH initiated the MATRICS in partnership with the FDA, industry and academia in an effort to improve the probability of identifying successful treatments for CIAS [Buchanan R W, Davis M, Goff D, et al. *Schizophr Bull* 2005; 31(1); 5-19]. One of the central aims of the MATRICS initiative was to identify the key domains of cognition to be assessed in studies of treatments for CIAS and to establish a cognitive battery that could be used to assess treatments. MATRICS identified seven domains of cognition that show significant impairment in schizophrenia and recommended using cognitive batteries that assess these 7 domains: speed of processing, verbal learning, working memory, reasoning and problem solving, visual learning, attention/vigilance and social cognition [Nuechterlein K H, Barch D M, Gold J M, Goldberg T E, Green M F, Heaton R K. *Schizophr Res* 2004; 72; 29-39].

A number of batteries have been developed to assess these domains [Keefe R S E, Haig G M, Marder S R, et al. *Schizophr Bull* 2016; 42(1); 19-33.] and have been used in clinical trials of cognition-enhancing drugs [Keefe R S E, Buchanan R W, Marder S R, et al. *Schizophr Bull* 2013; 39(2); 417-435]. The MATRICS Consensus Cognitive Battery (MCCB), Brief Assessment of Cognition in Schizophrenia (BACS), as well as computerised cognitive batteries such as CANTAB and CogState were developed to test cognition in patients with schizophrenia and have been used in clinical trials in the past. The MCCB has been used most frequently in clinical trials in CIAS. Higher values in the MCCB score indicate better cognitive function.

Previous studies in the field of schizophrenia or cognition explored the efficacy of a range of compounds for the treatment of CIAS, including α7 nicotinic acetylcholine receptor antagonists (such as encenicline, bradanicline [ABT-126], and nelonicline [TC-5619]), histamine-3 receptor antagonists (such as ABT-288), and phosphodiesterase-9 inhibitors (such as BI 409306). Of these potential treatments for CIAS, the only compound to establish proof-of-concept was encenicline; a Phase 2 study showed improvements in cognition compared with placebo, although this benefit was not maintained in subsequent Phase 3 trials.

Dysfunction of glutamatergic neurotransmission mediated by N-methyl-D-aspartate (NMDA) receptors is implicated in the aetiology of CIAS. [Lakhan S E, Caro M, Hadzimichalis N. *Front Psychiatry.* 2013; 4:52], [Lin C H, Lane H Y, Tsai G E. *Pharmacol Biochem Behav.* 2012; 100(4):665-677] Various strategies for enhancing glutamatergic transmission have been investigated in patients with schizophrenia; one approach involves increasing synaptic levels of glycine, a coagonist required for NMDA receptor-mediated signaling. [Hashimoto K. *Open Med Chem J.* 2010; 4:10-19. Pavia D C. *Current Opinion in Drug Discovery & Development.* 2009; 12:468-478.] Inhibitors of glycine transporter-1 (GlyT1) are thought to elevate synaptic glycine levels and consequently enhance glutamatergic neurotransmission and downstream neuroplasticity processes, and therefore represent a promising treatment strategy to address cognitive impairment in general and specifically when manifested as mild cognitive impairment, amnestic mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, prodromal Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, Korsakoff's psychosis or cognitive impairment associated with schizophrenia (CIAS), depression, epilepsy, schizo-affective disorder or bipolar disorder.

GlyT1 inhibitors have previously been investigated as potential treatments for patients with cognitive impairment. However, previous studies investigating the cognitive benefits of the GlyT1 inhibitor sarcosine, which were generally small and used various measures of cognitive improvement, have produced inconsistent results. [Chang C H, Lin C H, Liu C Y, Chen S J, Lane H Y. *J Psychopharmacol.* 2020; 34(5):495-505], [Lin C Y, Liang S Y, Chang Y C, et al. *World J Biol Psychiatry.* 2017; 18(5):357-368] Trials of bitopertin, another GlyT1 inhibitor, targeted positive and negative symptoms rather than CIAS and in most cases failed to show statistically significant improvements versus placebo [Bugarski-Kirola D, Blaettler T, Arango C, et al. *Biol Psychiatry.* 2017; 82(1):8-16], [Bugarski-Kirola D, Iwata N, Sameljak S, et al. *The Lancet Psychiatry.* 2016; 3(12):1115-1128]. Methodes and procedures for the efficacious use of GlyT1 inhibitors as a potential treatment for CIAS are therefore warranted.

WO2013/017657 discloses substituted bicyclo[3.1.0]hex-3-yl methanones as GlyT1 inhibitors, including example 50, which has the structure shown below (hereinafter "compound I"):

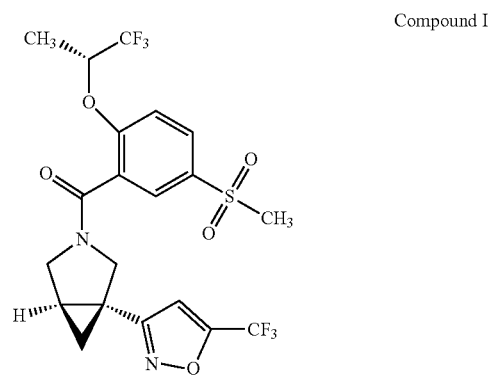 [SMILES: C[C@@H](Oc1ccc(S(C)(=O)=O)cc1C(=O)N1C[C@@H]2C[C@]2(c2cc(C(F)(F)F)on2)C1)C(F)(F)F]

Compound I ([5-(methylsulfonyl)-2-{[(2R)-1,1,1-trifluoropropan-2-yl]oxy}phenyl] {(1R,5R)-1-[5-(trifluoromethyl)-1,2-oxazol-3-yl]-3-azabicyclo[3.1.0]hex-3-yl}methanone)

However, WO2013/017657 does not provide specific indications on the administration of compound I, e.g. route or frequency of administration or effective doses etc, for the treatment of the various diseases mentioned therein. It now has been found that a specific dose or doses range are efficacious to improve cognition in patients suffering from CIAS. However, the same doses regimen was ineffective to improve cognition in patients suffering from Alzheimer's disease.

BRIEF SUMMARY OF THE INVENTION

In a phase 2 clinical trial, it has been found that compound I administered in certain doses to patients having schizophrenia improves cognitive performance when compared to placebo.

A first embodiment relates to compound I for use in the treatment of schizophrenia, characterized in that compound I is administered in a dose from 3 mg to 30 mg daily.

A further embodiment relates to compound I for use in the treatment of cognitive impairment associated with schizophrenia (CIAS), characterized in that compound I is administered in a dose from 3 mg to 30 mg daily.

A further embodiment relates to the use of compound I for the improvement of cognition in patients suffering from schizophrenia, characterized in that the compound is administered in a dose from 3 mg to 30 mg daily.

In further embodiments, compound I is administered in a dose from 10 mg to 25 mg.

DETAILED DESCRIPTION OF THE INVENTION

Figure 1:
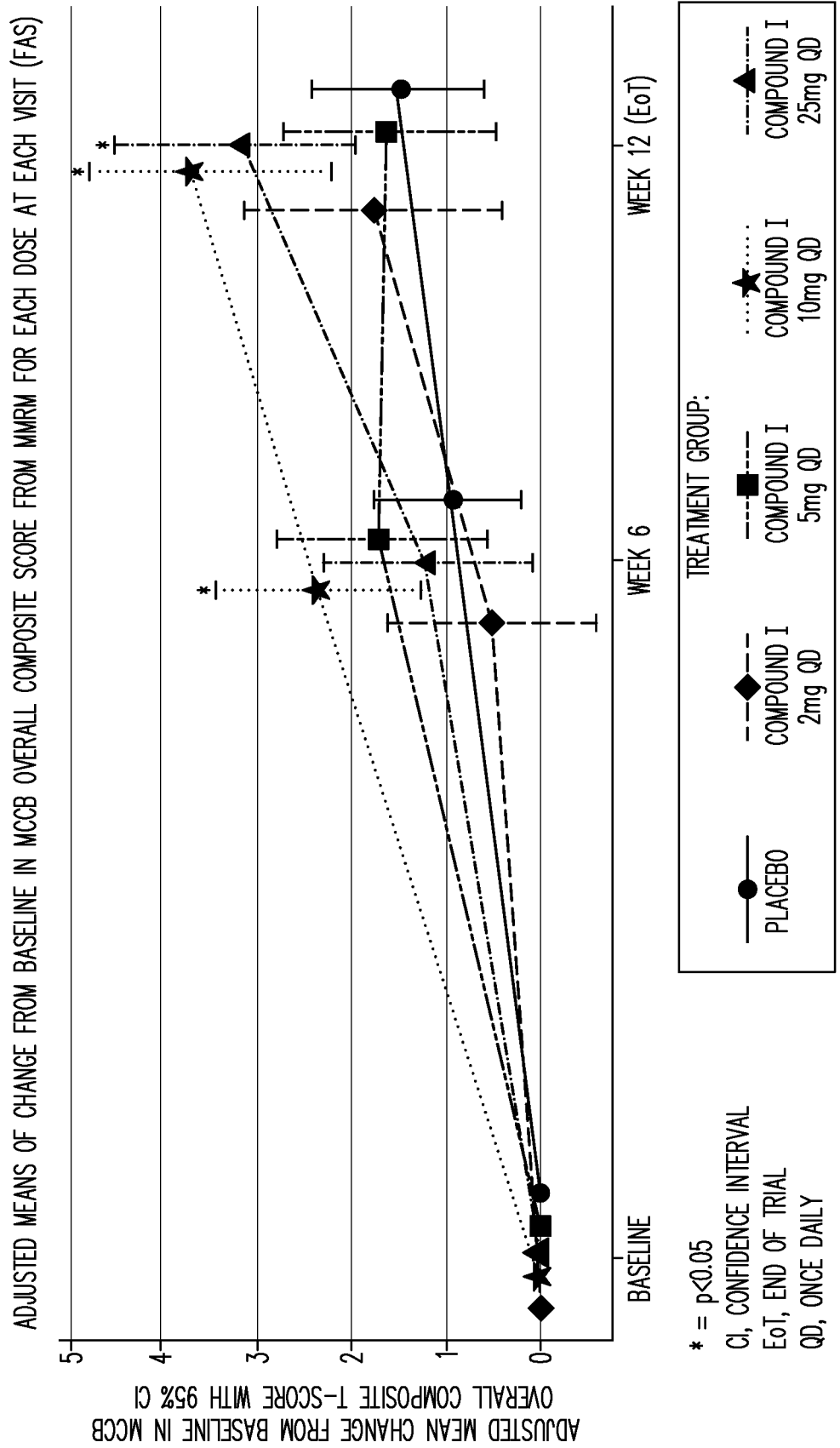
FIG. 1 shows the adjusted mean difference between each dose and placebo in change from baseline in MCCB overall composite score at each visit—MMRM, FAS (CIAS study).

A proof-of-clinical-concept (PoCC) and dose-finding study evaluated the efficacy, safety, and pharmacokinetics (PK) of compound I compared with placebo as add-on to standard of care in adult patients with schizophrenia. Observations in previous trials suggest that dose-response relationships for GlyT1 inhibitors can be complex, and selection of effective doses is challenging, with a loss of effect observed at higher doses. [Javitt D C. *Current Opinion in Drug Discovery & Development*. 2009; 12:468-478.6, 16], [Umbricht D. *Biol Psychiatry*. 2018; 84(6):394-395]

This trial in stable patients with schizophrenia demonstrated a non-flat dose-response curve for change from baseline at Week 12 in MCCB overall composite T-score with compound I of doses of 2 to 25 mg, suggesting improvements in cognition in this patient population. The largest improvements from baseline versus placebo were observed in the 10 and 25 mg dose groups; the 25 mg dose did not appear to provide an additional benefit over the 10 mg dose, although a formal comparison between dose groups was not conducted. Consistent results were seen when cognition was assessed using MCCB neurocognitive composite T-score.

These positive findings contrast with results of previous trials investigating novel treatments for CIAS, which have been generally negative. [Haig G M, Bain E E, Robieson W Z, Baker J D, Othman A A. *Am J Psychiatry*. 2016; 173(8): 827-835], [Walling D, Marder S R, Kane J, et al. *Schizophr Bull*. 2016; 42(2):335-343], [Brown D, Nakagome K, Cordes J, et al. *Schizophr Bull*. 2019; 45(2):350-359] Notably, the baseline cognitive profiles of the patient groups included in these previous trials, as assessed by mean baseline MCCB scores, were comparable to those of the population in the present study. Baseline MCCB scores in this study were approximately 1-2 SD below the mean for healthy individuals, in line with mean scores previously reported for chronically ill, clinically stable patients with schizophrenia. It is therefore unlikely that the positive findings of the present study were due to differences in the average baseline level of cognitive impairment.

Terms and Definitions

AD Alzheimer's Disease
ADAS-Cog11 The Alzheimer's Disease Assessment Scale—Cognitive Subscale 11-items
BACS Brief Assessment of Cognition in Schizophrenia
CANTAB The Cambridge Neuropsychological Test Automated Battery
CIAS Cognitive impairment associated with schizophrenia
CSB CogState Schizophrenia Battery
C-SSRS Columbia Suicide Severity Rating Scale
DSM-5 Diagnostic and Statistical Manual of Mental Disorders, $5^{th}$ edition
ECG Electrocardiogram
FAS Full Analysis Set
LOCF Last Observation Carried Forward
MATRICS Measurement And Treatment Research to Improve Cognition in Schizophrenia
MCCB MATRICS Consensus Cognitive Battery
MCPMod Multiple Comparison Procedures and Modelling
MMRM Mixed Model Repeated Measures
MMSE Mini-Mental State Exam
OC Observed Cases
PANSS Positive and Negative Syndrome Scale
PT Preferred Term
SCoRS Schizophrenia Cognition Rating Scale
SOC Standard of Care

Preferred Embodiments

A first embodiment relates to compound I for use in the treatment of schizophrenia, characterized in that compound I is administered in a dose from 3 mg to 30 mg daily.

A further embodiment relates to the use of compound I for the improvement of cognition in patients suffering from schizophrenia, characterized in that the compound is administered in a dose from 3 mg to 30 mg daily.

A further embodiment relates to the use of compound I for the improvement of cognition in patients suffering from schizophrenia, characterized in that the compound is administered in a dose from 3 mg to 30 mg daily and that the cognition is assessed using an overall composite score of one of the cognitive batteries that assess all 7 domains of cognition relevant for patients with schizophrenia.

A further embodiment relates to compound I for use in the treatment of cognitive impairment associated with schizophrenia (CIAS), characterized in that compound I is administered in a dose from 3 mg to 30 mg daily.

A further embodiment relates to compound I for use in the treatment of CIAS, characterized in that compound I is administered in a dose from 3 mg to 30 mg daily and that the cognition is assessed using at least one of the 7 domains of cognition relevant for patients with schizophrenia.

A further embodiment relates to compound I for use in the treatment of CIAS, characterized in that the compound is administered in a dose from 3 mg to 30 mg daily and that the cognition is assessed using an overall composite score of one of the cognitive batteries that assess all 7 domains of cognition relevant for patients with schizophrenia.

A further embodiment relates to compound I for use in the treatment of CIAS, characterized in that the compound is administered in a dose from 3 mg to 30 mg daily and that the cognition is assessed using the overall composite score of one of the cognitive batteries selected from MCCB, BACS, CANTAB and CogState Schizophrenia Battery (CSB).

A further embodiment relates to compound I for use in the treatment of CIAS, characterized in that compound I is administered in a dose from 3 mg to 30 mg daily and that the cognition is assessed using at least one of the 7 domains of cognition relevant for patients with schizophrenia as assessed in the MCCB.

A further embodiment relates to compound I for use in the treatment of CIAS, characterized in that compound I is administered in a dose from 3 mg to 30 mg daily and that the cognition is assessed using the MCCB overall composite score.

A further embodiment relates to compound I for use in the treatment of CIAS, characterized in that the compound is administered in a dose from 3 mg to 30 mg daily to improve cognition as rated by an overall composite score of one of the cognitive batteries that assess all 7 domains of cognition relevant for patients with schizophrenia.

A further embodiment relates to compound I for use in the treatment of CIAS, characterized in that compound I is administered in a dose from 3 mg to 30 mg daily to improve cognition as rated by the overall composite score on one of the cognitive batteries selected from MCCB, BACS, CANTAB and CogState.

A further embodiment relates to compound I for use in the treatment of CIAS, characterized in that compound I is administered in a dose from 3 mg to 30 mg daily to improve cognition as rated by the MCCB overall composite score.

A further embodiment relates to compound I for use in the treatment of CIAS, characterized in that compound I is administered in a dose from 3 mg to 30 mg daily to improve cognition as rated by at least one of the 7 domains of cognition relevant for patients with schizophrenia.

A further embodiment relates to compound I for use in the treatment of CIAS, characterized in that compound I is administered in a dose from 3 mg to 30 mg daily to improve cognition as rated by at least one of the 7 domains of cognition relevant for patients with schizophrenia as assessed in the MCCB.

A further embodiment relates to compound I for use in the treatment of CIAS, characterized in that compound I is administered in a dose from 3 mg to 30 mg daily to improve cognition as rated by at least 4 of the 7 domains of cognition relevant for patients with schizophrenia as assessed in the MCCB.

A further embodiment relates to compound I for use in the treatment of CIAS, characterized in that compound I is administered in a dose from 3 mg to 30 mg daily to improve cognition as rated by at least one of the 7 domains of cognition relevant for patients with schizophrenia as assessed in the MCCB, wherein the domain is selected from the group consisting of the Trail Making Test (processing speed), Neuropsychological Assessment Battery, mazes subtest (reasoning and problem solving), and the Wechsler Memory Scale, $3^{rd}$ edition (Wechsler Memory Scale), spatial span subtest (working memory).

In further embodiments, compound I is administered in a dose from 9 mg to 26 mg daily.

In further embodiments, compound I is administered in a dose from 5 mg to 25 mg daily.

In further embodiments, compound I is administered in a dose from 10 mg to 25 mg daily.

In further embodiments, compound I is administered in a dose of 10 mg daily.

In further embodiments, the daily dose is administered orally, e.g. as a one-time oral dose.

In additional embodiments, the invention is further characterized in that the patients are 50 years of age or younger.

In additional embodiments, the invention is further characterized in that the patients have no more than a "moderate severe" rating on the Positive and Negative Symptom Scale (PANSS) positive items P1, P3-P7 (item score≤5) and no more than a "moderate" rating on the PANS S positive item P2 (item score≤4).

In additional embodiments, the invention is further characterized in that the patients are on co-medication with an antipsychotic.

In additional embodiments, the invention is further characterized in that the patients are on co-medication with one or two antipsychotic(s).

In additional embodiments, the invention is further characterized in that the patients are on co-medication with one or two antipsychotic(s) with the provision that the antipsychotic is not clozapine.

In additional embodiments, the invention is further characterized in that the patients do not suffer by hemoglobinopathy such as thalassemia major or sickle-cell anaemia.

In additional embodiments, the invention is further characterized in that the patients have a haemoglobin level of 110 g/L or higher.

In additional embodiments, the invention is further characterized in that the patients have a haemoglobin level of 120 g/L in men or 115 g/l in women or higher.

The invention also relates to the use of compound I for the treatment of schizophrenia, CIAS or for the improvement of cognition in patients suffering from schizophrenia according to any one of the features of the embodiments above.

The invention also relates to a method of treating schizophrenia or CIAS according to any one of the features of the embodiments above.

The invention also relates to the use of compound I for the manufacture of a medicament for the treatment of schizophrenia or CIAS according to any one of the features of the embodiments above.

In a further aspect, the invention relates to the use of compound I for the treatment of schizophrenia or CIAS according to any one of the features of the embodiments above, wherein compound I is contained in a primary packaging, e.g. in a blister, vial, strip package, container, or sachet.

In a further aspect, the invention relates to a pharmaceutical composition for the use in the treatment of schizophrenia or CIAS according to any one of the features of the embodiments above, wherein the composition comprises 3 to 30 mg of compound I, optionally together with one or more inert carriers and/or diluents.

In a further aspect, the invention relates to a pharmaceutical composition comprising 3 to 30 mg of compound I, optionally together with one or more inert carriers and/or diluents.

In an embodiment of the pharmaceutical composition, the composition comprises 3 to 30 mg of compound I and at least one excipient selected from the group consisting of cellulose, lactose, croscarmellose and magnesium stearate.

In a further embodiment, the pharmaceutical composition is a tablet comprising 3 to 30 mg of compound I and at least one excipient selected from the group consisting of cellulose, lactose, croscarmellose and magnesium stearate.

In an additional embodiment, the pharmaceutical composition comprises 3 to 30 mg of compound I, microcrystalline cellulose, lactose monohydrate and magnesium stearate.

In additional embodiments, the pharmaceutical composition comprises 10 to 25 mg of compound I and is further defined as in any one of the embodiments above.

In additional embodiments, the pharmaceutical composition comprises 10 mg of compound I and is further defined as in any one of the embodiments above.

Clinical Trial—CIAS

Improvement of Cognitive Impairments Associated with Schizophrenia (CIAS): Study Design, Study Population Inclusion Criteria and Statistical Methods Cognitive impairments are a core feature of schizophrenia and have been shown to be a major determinant of poor functional outcome including drop-out from school and loss of employment. Antipsychotics, the standard-of-care, have minimal or no beneficial effects on cognition in patients with schizophrenia. As of yet, no drug has been approved for the treatment of cognitive impairment in schizophrenia.

This trial was designed to investigate whether compound I as an add-on therapy to antipsychotics (except clozapine) can improve cognitive symptoms in patients with schizophrenia.

This was a 12-week, multi-centre, multi-national, randomised, double-blind, double-dummy, placebo-controlled, parallel-group trial in patients with clinically stable schizophrenia.

Efficacy and safety of 4 oral doses of compound I (2, 5, 10 and 25 mg) and placebo once daily over 12 week treatment period were tested.

The primary endpoint was cognition assessed using the Measurement and Treatment Research to Improve Cognition in Schizophrenia (MATRICS) consensus cognitive battery (MCCB).

Study Medicine

Compound I and matching placebo were supplied as film-coated tablets at strength of 1, 5 and 25 mg.

Study Population

A total of 509 patients were randomised and treated with study medication, of which 480 patients (94.3%) completed the planned observation period, and 444 patients (87.2%) completed the planned treatment.

Key Inclusion Criteria

1) Men or women who are 18-50 years (inclusive) of age at time of consent with established schizophrenia (as per DSM-5) with the following clinical features:
   Outpatient, with no hospitalization for worsening of schizophrenia within 3 months (hospitalization for social management and/or day hospital programs within this time are acceptable) prior to randomization
   Medically stable over the prior 4 weeks and psychiatrically stable without symptom exacerbation within 3 months prior to randomization
   patients who have no more than a "moderate severe" rating on the Positive and Negative Symptom Scale (PANSS) positive items P1, P3-P7 (item score≤5) and no more than a "moderate" rating on the PANSS positive item P2 (item score≤4)
2) Current antipsychotic and concomitant psychotropic medications as assessed at Visit 1 must meet the criteria below:
   a. patients may have up to 2 antipsychotics (typical and/or atypical)
   b. patients must be maintained on current typical and/or atypical antipsychotics other than Clozapine and on current dose for at least 4 weeks prior to randomization and/or maintained on current long acting injectable antipsychotics and current dose for at least 3 months prior to randomization
   c. patients must be maintained on current concomitant psychotropic medications, anticholinergics, antiepileptics and/or lithium for at least 3 months prior to randomization and on current dose for at least 4 weeks prior to randomization.

Key Exclusion criteria

1) Patients who have a categorical diagnosis of another current major psychiatric disorder
2) Diseases of the central nervous system that may impact the assessment of the cognitive tests as per investigator's opinion
3) A movement disorder due to antipsychotic treatment not currently controlled with treatment for extrapyramidal symptoms or another movement disorder (e.g. Parkinson's disease)
4) Patients participating in any formal cognitive remediation program for at least 4 sessions within the last 4 weeks prior to randomization
5) Patients who have been on BI 409306, encenicline or other investigational drug testing effects on cognition in schizophrenia within the last 6 months prior to randomization or who have previously been on bitopertin
6) Patients who have participated in a clinical trial with repeated MCCB assessments within the last 6 months prior to randomization
7) Patients who required change in ongoing stable benzodiazepine or sleep medication regimen within the last 4 weeks prior to randomization
8) Patients who have been treated with Clozapine within 6 months prior to randomization
9) Patients taking strong or moderate CYP3A4 inhibitors or inducers within the last 30 days prior to randomization
10) Any suicidal behavior in the past 2 years (i.e. actual attempt, interrupted attempt, aborted attempt, or preparatory acts or behavior) prior to randomization
11) Any suicidal ideation of type 4 or 5 in the Columbia Suicidal Severity Rating Scale (C-SSRS) in the past 3 months (i.e. active suicidal thought with intent but without specific plan, or active suicidal thought with plan and intent) prior to randomization
12) In the judgment of the investigator any clinically significant finding of the physical examination (including blood pressure, pulse rate and ECG) or laboratory value (as measured by the central laboratory at visit 1) that would jeopardize the patient's safety while participating in the trial and their capability to participate
13) Any symptomatic/unstable/uncontrolled or clinically relevant concomitant disease or any other clinical condition that would jeopardize the patient's safety while participating in the trial and capability to participate in the trial as per investigator's opinion.

14) Hemoglobin less than 120 g/L (12 g/dL) in men or 115 g/L (11.5 g/dL) in women OR history of hemoglobinopathy such as thalassemia major or sickle-cell anemia Randomization Patients eligible for the trial were randomly assigned, in a 1:1:1:1:2 ratio to either 2 mg compound I
5 mg compound I
10 mg compound I
25 mg compound I
Placebo Statistical Methods An MCPMod approach combined with MMRM was used to establish the proof of concept in this trial.

The null hypothesis was that there was a flat dose-response pattern across placebo and any dose of compound I within the tested dose range on the mean change in the MCCB overall composite score from baseline to Week 12. The alternative hypothesis was that there was a non-flat dose-response pattern indicating a benefit of compound I versus placebo.

The MCPMod procedure allowed for the simultaneous evaluation of different plausible dose-response patterns while protecting the overall probability of type I error (one-sided alpha of 0.05). The pre-specified dose-response patterns were:

Linear
 No assumptions needed
Linear in Log
 No assumptions needed
Emax
 20% of the maximum effect is achieved at 2 mg
Sigmoid Emax
 25% of the maximum effect is achieved at 5 mg
 75% of the maximum effect is achieved at 10 mg
Logistic
 10% of the maximum effect is achieved at 5 mg
 50% of the maximum effect is achieved at 10 mg
Beta Model
 75% of the maximum effect is achieved at 2 mg
 87.5% of the maximum effect is achieved at 5 mg
 25% of the maximum effect is achieved at 25 mg
 Maximum effect achieved at 10 mg
 Scalar parameter=26

For the sample size calculation, the maximum standardised effect size was assumed to be 0.35.

The statistical analyses were based on the following patient populations:

Randomised Set (RS)

The RS consisted of all patients who were screened for the trial and who were randomised to trial treatment, regardless of whether any trial treatment was administered.

Treated Set (TS)

The TS included all patients who were randomised and were treated with ≥1 dose of trial medication. Patients in the TS were analysed according to the actual trial medication they received at randomisation. The TS was used for analyses of safety, demographics, and baseline characteristics.

Full Analysis Set (FAS)

The FAS included all patients in the TS who had a non-missing baseline measurement and ≥1 non-missing post-baseline and on-treatment measurement for primary or secondary efficacy endpoint. Patients in the FAS were analysed according to the ITT principle, i.e. according to their randomised trial medication. The FAS was used for analyses of efficacy.

Results

Demographic Data and Baseline Characteristics:

Treatment groups were well-balanced on demographics, baseline characteristics, and baseline efficacy variables. The patient population was 64.6% male with a mean age of 37.1 years (SD 7.7). Approximately half the patients were White (46.6%) and about a quarter each were Asian (28.5%) or Black (23.4%). Hispanic patients made up 8.1% of the trial population. Most patients were located in North America (43.4%), followed by Europe (29.9%) and then Asia (26.7%).

The mean time since diagnosis in the trial population was 12.14 years (SD 7.81). Baseline efficacy measures were in line with expected values for this patient population: the mean MCCB overall composite score was 31.5 (SD 13.2), the mean MCCB neurocognitive composite score was 33.3 (SD 12.9), and the mean PANSS total score was 60.8 (SD 15.1).

Primary Efficacy Endpoint:

The primary endpoint of this trial was the change from baseline in cognitive function as measured by the MCCB overall composite score after 12 weeks of treatment. The primary efficacy analysis was based on the full analysis set (FAS).

The trial demonstrated proof of clinical concept, as the null hypothesis of a flat dose-response relationship was rejected for the primary endpoint, the change from baseline in MCCB overall composite score after 12-weeks of treatment (Table 1). The adjusted mean change from baseline at Week 12 in MCCB overall composite score had a nominal p-value<0.05 for the 10 mg and 25 mg treatment groups versus placebo (Table 2).

TABLE 1

MCPMod test for non-flat dose-response curve of change from baseline in MCCB overall composite score at Week 12 - FAS

|  | sigEmax | logistic | emax | linear | linlog | betaMod |
|---|---|---|---|---|---|---|
| t-Stat | 2.9827 | 2.7658 | 2.7531 | 2.5522 | 2.5571 | 1.2420 |
| Adjusted p-value | 0.0038* | 0.0085* | 0.0089* | 0.0145* | 0.0148* | 0.2280 |

Critical value for t-Stat: 2.062, alpha =0.050, one-sided, * significant shape

TABLE 2

Comparison of change from baseline in MCCB overall composite score at Week 12 by treatment group-MMRM, FAS

|  | Compound I | | | | Placebo |
|---|---|---|---|---|---|
|  | 2 mg | 5 mg | 10 mg | 25 mg | |
| Number of patients, N | 79 | 80 | 82 | 83 | 163 |
| Change from baseline | | | | | |
| Adjusted mean (SE) | 1.784 (0.681) | 1.641 (0.666) | 3.486 (0.641) | 3.234 (0.641) | 1.504 (0.458) |
| 95% CI | (0.447, 3.121) | (0.333, 2.949) | (2.226, 4.746) | (1.975, 4.494) | (0.604, 2.404) |
| Comparison vs. Placebo | | | | | |
| Adjusted mean (SE) | 0.280 (0.821) | 0.137 (0.807) | 1.982 (0.788) | 1.730 (0.788) | |
| 95% CI | (−1.332, 1.892) | (−1.450, 1.724) | (0.434, 3.530) | (0.181, 3.280) | |
| p-value | 0.733 | 0.866 | 0.012 | 0.029 | |

Model includes fixed, categorical factors of planned treatment, analysis visit, and planned treatment by analysis visit interaction, as well as the continuous fixed covariate of baseline value and baseline value by analysis visit interaction. Subject is treated as random effect. Unstructured covariance structure was used to fit the mixed model. Kenward-Roger was used to model degrees of freedom.

See FIG. 1.

Further Endpoints Relevant to Cognition:

1) Change from baseline in MCCB neurocognitive composite score at Week 12: the neurocognitive composite score is calculated without the social cognition domain, i.e. derived from only 6 of the 7 cognitive domains in the MCCB.

It was analysed in the same way as the primary endpoint and the results were generally consistent with the primary endpoint. The adjusted mean change from baseline at Week 12 in MCCB neurocognitive composite score was also consistent with the primary endpoint. A larger change from baseline was observed in the 10 mg and 25 mg treatment groups compared with the placebo group.

2) Change from baseline in MCCB test and domain t-scores at Week 12

Majority of the MCCB tests contributed to the overall composite score. The largest separation from placebo was seen on the Trail Making Test (processing speed), Neuropsychological Assessment Battery, mazes subtest (reasoning and problem solving), and the Wechsler Memory Scale, $3^{rd}$ edition (Wechsler Memory Scale), spatial span subtest (working memory).

Endpoints of Safety:

Safety was assessed based on the frequency of AEs, recording of vital signs, ECG measurements, standard laboratory tests, physical examination, neurological examination, as well as PANSS and C-SSRS questionnaires.

Approximately 50% of patients in any treatment arm reported on-treatment AEs, with similar proportions reporting AEs in each treatment arm. No dose-dependency was observed for overall AEs or drug-related AEs. AEs of severe intensity, AEs leading to premature discontinuation, protocol-specified AESIs, and SAEs were reported at low frequencies in all treatment groups. There were no deaths. The most frequently observed AE was headache. Headache was reported more frequently in all dose groups of compound I than placebo. Somnolence was more common in the 5 mg and 10 mg dose groups compared with the 2 mg and 25 mg dose groups and placebo. In general, gastrointestinal disorders (including constipation, nausea, vomiting, upper abdominal pain, and diarrhoea) were reported more frequently with compound I than placebo. Approximately 10% of patients reported psychiatric disorders; these were balanced across all treatment groups. No significant differences in suicidal ideation and behaviour, as assessed using C-SSRS, were observed between compound I and placebo. There was no worsening of schizophrenia (assessed by PANSS total score).

A slight dose-dependent decrease from baseline in haemoglobin was observed at the last on-treatment value (mean change from baseline [SD]; 2 mg: −0.2 g/L [7.3]; 5 mg: −0.7 g/L [8.3]; 10 mg: 3.3 g/L [7.8]; 25 mg: 4.5 g/L [7.7]; placebo: −0.5 g/L [8.2]; relative change from baseline; 2 mg: −0.1%; 5 mg: −0.5%; 10 mg: −2.3%; 25 mg: −3.2%; placebo: −0.4%). Decrease in haemoglobin is a known class effect of GlyT1 inhibitors. No clinically relevant changes from baseline or differences between treatment groups were observed for other laboratory parameters, vital signs, ocular parameters, or electrocardiogram.

Dose Considerations

Schizophrenia is characterised by abnormalities in glutamatergic pathways related to NMDA receptor hypofunction. Together with glutamate, glycine acts as co-agonist at the NMDA receptor by binding to its glycine binding site. As glycine levels in cognition relevant brain areas are regulated by GlyT1, inhibition of GlyT1 leads to an increase of glycine levels in the synaptic cleft. This should translate into a normalisation of NMDA receptor function in patients and thus improvement of cognitive performance. As known for other modulators of the glutamatergic system, an overactivation of the NMDA receptor might lead to a counter-regulation of the neuronal network. Therefore, in order to treat cognitive deficits related NMDA receptor hypofunction, the activation of the NMDA receptor by the co-agonist glycine needs to be in an optimal range. This hypothesis is supported by other clinical studies, and by animal studies that showed bell-shaped dose-response in animal cognition tests [Javitt D C. *Curr Opin Drug Discov Dev* 2009; 12(4); 468-478], [D'Souza D C, Carson R E, Driesen B, et al. *Biol Psychiatry* 2018; 84(6); 413-421], [Umbricht D. *Biol Psychiatry* 2018; 84; 394-395].

In animal cognition tasks, efficacy of compound I was achieved at doses that increased CSF glycine by approximately 50%, requiring CSF levels of compound I to be in the range of 1-2× GlyT1 $IC_{50}$. In a proof of clinical mechanism trial in healthy volunteers, these criteria were met by the 10 mg dose.

In the Phase II trial, the dose of 10 mg separated best from placebo in terms of the primary endpoint and contained a greater proportion of responders compared with placebo or the other active treatment groups (Table 3).

Dose 2 mg was ineffective, e.g., effect on cognition was in the range of placebo response Dose 5 mg numerically improved cognition in Asian subpopulation (not statistically powered or controlled for multiplicity) but no other analyses Dose 25 mg showed efficacy less consistent across analyses than the 10 mg dose.

It can be concluded that the 2 mg dose is ineffective, and that there are indications that the 10 mg dose is more likely to provide clinically relevant improvement in cognition than doses higher than 25 mg.

TABLE 3

Proportion of responders defined by change from baseline in MCCB overall composite score at Week 12-logistic regression, FAS

|  | | | Responders | Comparison vs. placebo | |
| --- | --- | --- | --- | --- | --- |
|  | N | n | [%] | Odds ratio | 95% CI |
| ≥3 | | | | | |
| Placebo | 152 | 64 | 42.1 | | |
| 2 mg compound I | 67 | 31 | 46.3 | 1.184 | (0.664, 2.111) |
| 5 mg compound I | 71 | 30 | 42.3 | 1.006 | (0.569, 1.780) |
| 10 mg compound I | 78 | 48 | 61.5 | 2.200 | (1.259, 3.845) |
| 25 mg compound I | 78 | 37 | 47.4 | 1.241 | (0.717, 2.148) |
| ≥4 | | | | | |
| Placebo | 152 | 52 | 34.2 | | |
| 2 mg compound I | 67 | 27 | 40.3 | 1.298 | (0.718, 2.347) |
| 5 mg compound I | 71 | 27 | 38.0 | 1.180 | (0.658, 2.118) |
| 10 mg compound I | 78 | 41 | 52.6 | 2.131 | (1.221, 3.718) |
| 25 mg compound I | 78 | 32 | 41.0 | 1.338 | (0.763, 2.347) |

TABLE 3-continued

Proportion of responders defined by change from baseline in MCCB overall composite score at Week 12-logistic regression, FAS

|  | N | n | Responders [%] | Comparison vs. placebo Odds ratio | 95% CI |
|---|---|---|---|---|---|
| ≥5 | | | | | |
| Placebo | 152 | 44 | 28.9 | | |
| 2 mg compound I | 67 | 24 | 35.8 | 1.370 | (0.744, 2.522) |
| 5 mg compound I | 71 | 23 | 32.4 | 1.176 | (0.640, 2.161) |
| 10 mg compound I | 78 | 35 | 44.9 | 1.998 | (1.133, 3.524) |
| 25 mg compound I | 78 | 31 | 39.7 | 1.619 | (0.913, 2.872) |

Clinical Trial—AD

Improvement of Cognitive Impairments Due to Alzheimer's Disease: Study Design, Study Population Inclusion Criteria and Statistical Methods Alzheimer's Disease (AD) is the most common cause of dementia and accounts for 50 to 70% of all dementia cases. Cognitive impairments are a core feature of AD. In the early stage of the clinical disease manifestation cardinal symptoms are characterized by an impairment of episodic memory and other cognitive domains, like executive function, orientation and judgment. This is followed by a progressive decline in the ability to perform activities of daily living and the appearance of behavioural changes and/or psychiatric symptoms (mood disturbances, hallucinations, personality changes). Currently approved AD treatments (acetylcholinesterase inhibitors, memantine) are used to treat the impairments in memory and function.

This trial was designed to investigate whether compound I either alone as monotherapy or as an add-on therapy to acetylcholinesterase inhibitors can improve cognitive symptoms in patients with AD.

This was a 12-week, multi-centre, multi-national, randomised, double-blind, double-dummy, placebo-controlled, parallel-group trial in patients with mild to moderate dementia due to AD.

Efficacy and safety of 4 oral doses of compound I (2, 5, 10 and 25 mg) and placebo once daily over 12 week treatment period were tested.

The primary endpoint was change from baseline in ADAS-Cog11 (Alzheimer's Disease Assessment Scale-cognitive subscale) total score after 12-week treatment. (Lower values in the ADAS-Cog11 score indicate better cognitive function.)

Study Medicine

Compound I and matching placebo were supplied as film-coated tablets at strength of 1, 5 and 25 mg.

Study Population

A total of 610 patients were randomised and treated with study medication, of which 574 patients (94.1%) completed the planned treatment period.

Key Inclusion Criteria
1) Diagnosis of mild-to-moderate Alzheimer's Disease Dementia according to the recommendations from the National Institute on Aging-Alzheimer's Association workgroups on diagnostic guidelines for Alzheimer's disease.
2) Male or female patients at least 55 years of age. Patients older than 85 years could be included based on an acceptable general health status, (e.g. concomitant diseases, physical capability to follow the required study procedures (visits etc.)) at discretion of the investigator
3) MMSE score of 15-26 at screening (Visit 1).
4) Concomitant use of AChEIs allowed but not required.

Key Exclusion Criteria
1) Dementia secondary to disorders other than Alzheimer's Disease Dementia.
2) Any central nervous system disease other than AD which according to the investigator may be associated with worsening of cognition.
3) Any suicidal behaviour in the past 2 years (i.e. actual attempt, interrupted attempt, aborted attempt, or preparatory acts or behaviour).
4) Any suicidal ideation of type 4 or 5 in the C-SSRS in the past 3 months (i.e. active suicidal thought with intent but without specific plan, or active suicidal thought with plan and intent).
5) Previous participation in investigational drug studies of dementia of Alzheimer's Type within three months prior to screening. Patients having received any active treatment in studies targeting disease modification of AD are excluded.

Randomization

Patients eligible for the trial were randomly assigned, in a 1:1:1:1:1 ratio to either
  2 mg compound I
  5 mg compound I
  10 mg compound I
  25 mg compound I
  Placebo Statistical Methods An MCPMod approach combined with MMRM was used to test for the proof of concept in this trial.

The null hypothesis was that there was a flat dose-response pattern across placebo and any dose of compound I within the tested dose range on the primary endpoint. The alternative hypothesis was that there was a non-flat dose-response pattern indicating a benefit of compound I versus placebo.

The MCPMod procedure allowed for the simultaneous evaluation of different plausible dose-response patterns while protecting the overall probability of type I error (one-sided alpha of 0.05). The pre-specified dose-response patterns were:

Linear
  No assumptions needed
Linear in Log
  No assumptions needed
Emax
  20% of the maximum effect is achieved at 2 mg
Sigmoid Emax
  25% of the maximum effect is achieved at 5 mg
  75% of the maximum effect is achieved at 10 mg
Logistic
  10% of the maximum effect is achieved at 5 mg
  50% of the maximum effect is achieved at 10 mg
Beta Model
  75% of the maximum effect is achieved at 2 mg
  87.5% of the maximum effect is achieved at 5 mg
  25% of the maximum effect is achieved at 25 mg
  Maximum effect achieved at 10 mg
  Scalar parameter=26

For the sample size calculation, the maximum standardised effect size was assumed to be 0.35.

The statistical analyses were based on the following patient populations:

Randomised Set (RS)

The RS consisted of all patients who were screened for the trial and who were randomised to trial treatment, regardless of whether any trial treatment was administered.

Treated Set (TS)

The TS included all patients who were randomised and were treated with ≥1 dose of trial medication. Patients in the TS were analysed according to the actual trial medication they received at randomisation. The TS was used for analyses of safety, demographics, and baseline characteristics.

Full Analysis Set (FAS)

The FAS included all patients in the TS who had a non-missing baseline measurement and ≥1 non-missing post-baseline and on-treatment measurement for primary or secondary efficacy endpoint. Patients in the FAS were analysed according to the ITT principle, i.e. according to their randomised trial medication. The FAS was used for analyses of efficacy.

Results

Demographic Data and Baseline Characteristics:

Demographic data in the trial were generally balanced across the treatment groups. The mean patient age was 72.9 years (SD 7.7, min 55 years, and max 89 years). Slightly more women than men took part in this trial (46.9% male and 53.1% female).

Patients were predominantly White (81.1%), 9.5% of patients were Asian, 4.9% Black or African American, and 1.0% Native Hawaiian or Other Pacific Islander. Most patients were from Europe (60.7%) or North America (30.5%), 8.9% were from Asia.

The mean time since the first onset of symptoms or the diagnosis was 2.32 years (SD 2.50). Overall, 34.9% of patients had a family history of AD in a first-degree relative.

In the trial, 72.0% of patients had mild AD (MMSE 20-26) and 28.0% had moderate AD (MMSE 15-19). The median MMSE score was 22, 52.8% of patients had an MMSE score≥22 and 47.0% of patients<22. At baseline, 62.5% of patients were using an acetylcholinesterase inhibitor. Overall, 49.7% of patients carried the APOE e4 allele.

Primary Efficacy Endpoint:

The primary endpoint was the change from baseline in ADAS-Cog11 total score after 12 weeks of treatment. The analyses for PoC and dose-finding were done using the MCPmod technique for MMRM.

None of the tested 6 models for dose-response curves was statistically significant, no dose response relation was observed (Table 4). The subsequent prediction of the optimal dose could therefore not be performed. MMRM estimates for change from baseline at Week 12 are shown in Table 5. The patients in the compound I treatment groups as well as those in the placebo group showed similar ADAS-Cog11 results at Week 12 and at baseline. The adjusted mean change from baseline was between −0.08 and 0.69 (SE 0.41) for all treatment groups.

Sensitivity analyses using ANCOVA based on FAS with LOCF or OC are consistent with the main analyses.

TABLE 4

MCPmod test for non-flat dose-response curve of change from baseline in ADAS-Cog11 total score at Week 12 - FAS (OC)

|  | Linear | logistic | emax | sigEmax | linlog | betaMod |
|---|---|---|---|---|---|---|
| t-Stat | 0.0501 | −0.1024 | −0.4898 | −0.5233 | −0.5504 | −1.2587 |
| Adjusted p-value | 0.7646 | 0.8199 | 0.9225 | 0.9287 | 0.9335 | 0.9931 |

Critical value for t-Stat: 2.084, alpha = 0.05, one-sided

TABLE 5

Comparison of change from baseline in ADAS-Cog11 total score at Week 12 by treatment group-MMRM analysis-FAS (OC)

|  | Compound I | | | | Placebo |
|---|---|---|---|---|---|
|  | 2 mg | 5 mg | 10 mg | 25 mg |  |
| Patients with data at Week 12, N | 114 | 114 | 113 | 115 | 116 |
| Change from baseline |  |  |  |  |  |
| Adjusted mean | −0.02 | 0.23 | 0.69 | −0.08 | −0.07 |
| (SE) | (0.41) | (0.41) | (0.41) | (0.41) | (0.41) |
| 95% CI | (−0.82, 0.79) | (−0.57, 1.04) | (−0.12, 1.50) | (−0.89, 0.72) | (−0.87, 0.74) |
| Comparison vs. Placebo |  |  |  |  |  |
| Adjusted mean | 0.05 | 0.30 | 0.76 | −0.02 |  |
| (SE) | (0.58) | (0.58) | (0.58) | (0.58) |  |
| 95% CI | (−1.09, 1.18) | (−0.84, 1.44) | (−0.38, 1.90) | (−1.16, 1.12) |  |
| p-value | 0.934 | 0.604 | 0.193 | 0.974 |  |

Model includes fixed, categorical factors of planned treatment (p-value=0.3425), analysis visit (p-value=0.7890), baseline MMSE stratification factor (≥20, <20) (p-value≤0.0001), and planned treatment by analysis visit interaction (p-value=0.7534), as well as the continuous fixed covariate of baseline value (p-value≤0.0001) and baseline value by analysis visit interaction (p-value=0.1185).

The following covariance structure has been used to fit the mixed model: Unstructured Kenward-Roger was used to model degrees of freedom.

Figure 2:
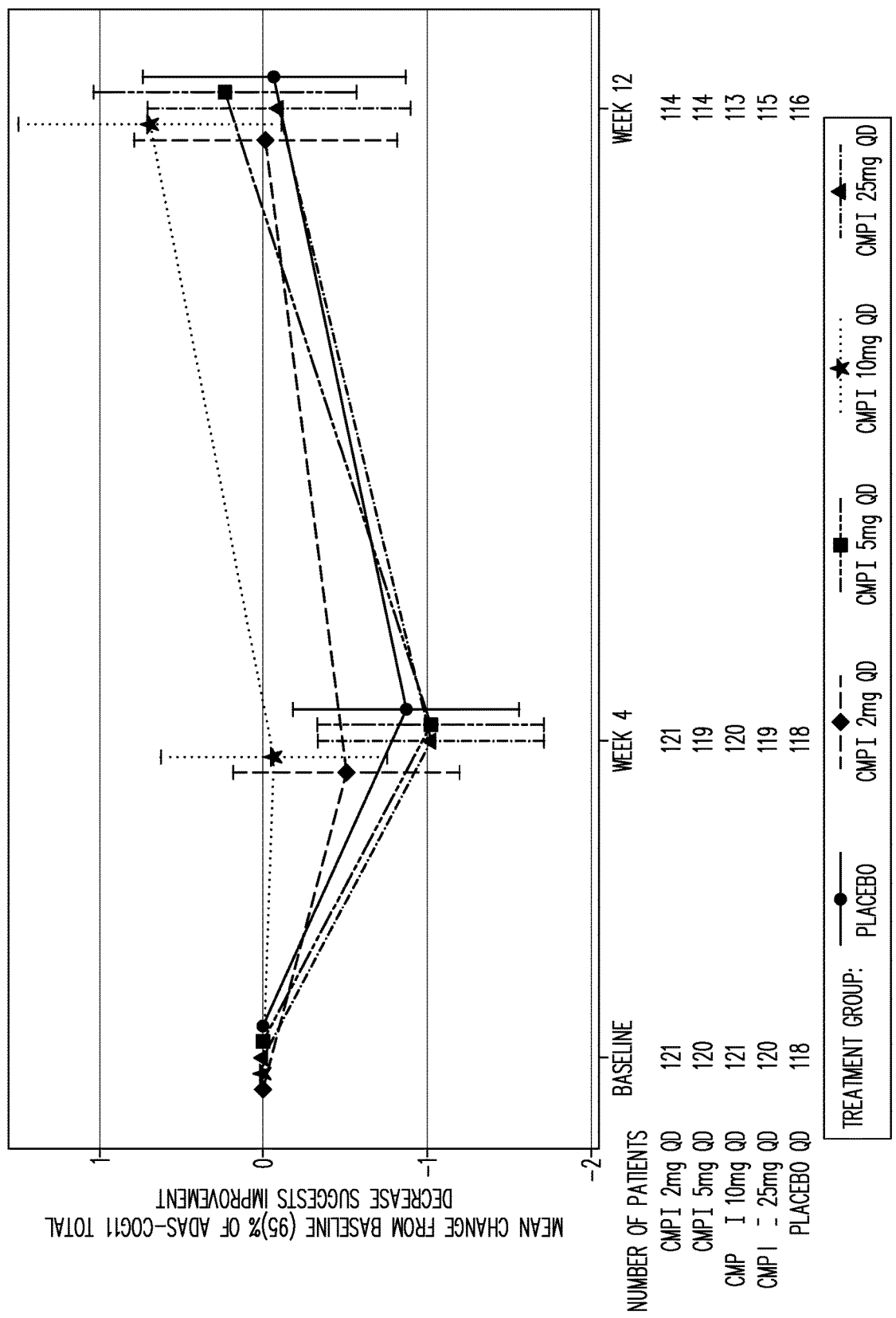
FIG. 2 shows the adjusted mean change from baseline in ADAS-Cog11 total score for each dose and visit (MMRM)-FAS (OC) (AD study). "CMP I" refers to compound I.

See FIG. 2.

Further Endpoints Relevant to Cognition:

For secondary efficacy endpoints of change from baseline in Activities of daily living (ADCS-ADL) and Clinician's Interview-Based Impression of Change (CIBIC+) as well as further endpoints of change from baseline on a derived cognitive composite, COWAT (Controlled Oral Word Association Test), VFT (Verbal Fluency Test), Coding, and Digit Span Backwards no treatment differences indicative of a benefit were found.

Endpoints of safety:

Safety assessments included the frequency of AEs, recording of vital signs, ECG measurements, standard laboratory tests, physical examination, and C-SSRS questionnaires.

Overall, 47.9% of patients reported at least 1 AE during the trial. The overall frequency of AEs did not show any meaningful differences between the treatment groups. The most frequently reported AEs with an overall frequency≥10% at the SOC level were 'nervous system disorders' (12.8%), 'infections and infestations' (12.3%), and 'gastrointestinal disorders' (11.0%). At PT level, AEs with an overall frequency≥3% were headache (5.4%), diarrhoea (3.9%), dizziness (3.9%), nasopharyngitis (3.1%), and nausea (3.1%). Most reported AEs were of mild or moderate intensity. In total, 15 patients (2.5%) had AEs of severe intensity. Overall, investigator-defined drug-related AEs were reported for 104 patients (17.0%). Frequencies were similar across the different treatment groups. Adverse events leading to treatment discontinuation were reported for 20 patients (3.3%) in total. The most frequently reported SOC was 'psychiatric disorders' (4 patients, 0.7%), followed by 'gastrointestinal disorders' (3 patients, 0.5%). All PTs were reported by single patients only.

There was 1 patient with a protocol-prespecified AESI. One patient in the placebo group was reported with drug-induced liver injury, the event met the AESI criterion of ALT levels>10× ULN.

In total, 22 patients (3.6%) were reported with at least one SAE. No patient died due to an AE. SAE frequencies were similar across the different treatment groups. The only SAE reported for≥0.5% of patients overall was 'fall' (4 patients, 0.7%).

In total, 15 patients (2.5%) reported suicidal ideations of Grade 1 to 3, i.e. without intent to act. No patients reported suicidal ideations of Grades 4 or 5, i.e. active ideation.

A dose-dependent decrease of haemoglobin levels was observed. The maximum effect was a decrease of 5.7% observed in the 25 mg compound I treatment group (placebo: slight decrease of 0.5%). Particularly in the 25 mg compound I group, the frequency of patients with a shift from normal haemoglobin levels at baseline to a low level on treatment was higher than in the other treatment groups.

There were no other clinically relevant changes from baseline for any of the safety laboratory parameters or of vital signs.

Pharmaceutical Composition—Tablets

Examples of tablet formulations are provided in Table 6:

TABLE 6

Qualitative and quantitative composition of tablet formulations comprising compound I

| Ingredient | Quantity [%] | | | Function |
| --- | --- | --- | --- | --- |
| | 1 mg dose | 5 mg dose | 25 mg dose | |
| Compound I | 1.25 | 6.25 | 6.25 | API |
| Cellulose, microcrystalline | 62.00 | 59.30 | 59.30 | Filler |
| Lactose monohydrate | 32.75 | 30.45 | 30.45 | Filler |
| Croscarmellose sodium | 3.00 | 3.00 | 3.00 | Disintegrant |
| Magnesium stearate (intra granular) | 0.5 | 0.5 | 0.5 | Lubricant |
| Magnesium stearate (extra granular) | 0.5 | 0.5 | 0.5 | Lubricant |
| Total (%) | 100.00 | 100.00 | 100.00 | — |
| Total tablet weight | 80.00 mg | 80.00 mg | 400.00 mg | — |

What we claim:

1. A method for improving cognition in schizophrenia patients or treating cognitive impairment associated with schizophrenia (CIAS), comprising administering compound (I) to a patient in need thereof

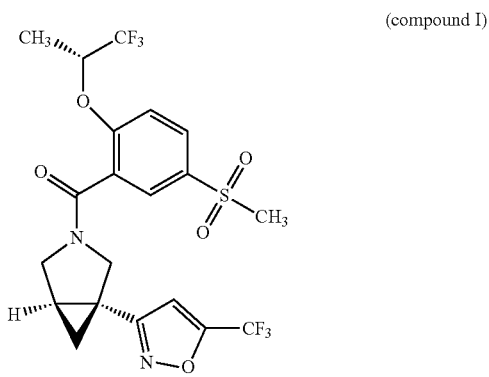 [SMILES: C[C@@H](Oc1ccc(S(C)(=O)=O)cc1C(=O)N1C[C@@H]2C[C@]2(c2cc(C(F)(F)F)on2)C1)C(F)(F)F]

(compound I)

wherein compound (I) is administered in a dose from 10 mg to 25 mg daily.

2. The method according to claim 1, wherein the method is for improving cognition in patients with schizophrenia.

3. The method according to claim 1, wherein the method is for treatment of cognitive impairment associated with schizophrenia (CIAS).

4. The method according to claim 2, wherein the cognition is assessed using at least one of 7 domains of cognition relevant for patients with schizophrenia.

5. The method according to claim 2, wherein the cognition is assessed using an overall composite score of one of 7 domains of cognition relevant for patients with schizophrenia.

6. The method according to claim 2, wherein the cognition is assessed using an overall composite score of one or more cognitive batteries selected from the group consisting of MATRICS Consensus Cognitive Battery (MCCB), Brief Assessment of Cognition in Schizophrenia (BACS), Cambridge Neuropsychological Test Automated Battery (CANTAB) and CogState Schizophrenia Battery (CSB).

7. The method according to claim 6, wherein the cognition is assessed using at least one of the 7 domains of cognition relevant for patients with schizophrenia as assessed in the MCCB.

8. The method according to claim 6, wherein the cognition is assessed using at least 4 of the 7 domains of cognition relevant for patients with schizophrenia as assessed in the MCCB.

9. The method according to claim 6, wherein the cognition is assessed using the MCCB overall composite score.

10. The method according to claim 6, wherein the cognition is assessed using at least one of the 7 domains of cognition relevant for patients with schizophrenia as assessed in the MCCB, wherein the domain is selected from the group consisting of the Trail Making Test (processing speed), Neuropsychological Assessment Battery, mazes subtest (reasoning and problem solving), and the Wechsler Memory Scale, spatial span subtest (working memory).

11. The method according to claim 1, wherein the patient is 50 years of age or younger.

12. The method according to claim 1, wherein the patient is on co- medication with an antipsychotic.

13. The method according claim 1, wherein the compound is administered in a dose of 10 mg daily.

14. A method for treating cognitive impairment associated with schizophrenia (CIAS), comprising administering to a patient in need thereof a compound of formula (I)

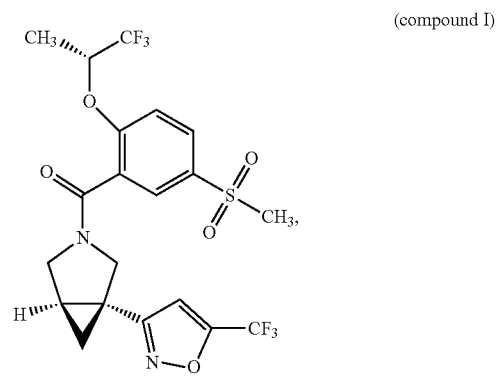 [SMILES: C[C@@H](Oc1ccc(S(C)(=O)=O)cc1C(=O)N1C[C@@H]2C[C@]2(c2cc(C(F)(F)F)on2)C1)C(F)(F)F]

(compound I)

wherein compound (I) is administered in a dose from 10 mg to 25 mg daily.

15. The method according claim 14, wherein the compound is administered in a dose of 10 mg daily.

16. The method according to claim 14, wherein the cognition is assessed using at least one of 7 domains of cognition relevant for patients with schizophrenia.

17. The method according to claim 14, wherein the cognition is assessed using an overall composite score of one of 7 domains of cognition relevant for patients with schizophrenia.

18. The method according to claim 14, wherein the cognition is assessed using an overall composite score of one or more cognitive batteries selected from the group consisting of MATRICS Consensus Cognitive Battery (MCCB), Brief Assessment of Cognition in Schizophrenia (BACS), Cambridge Neuropsychological Test Automated Battery (CANTAB) and CogState Schizophrenia Battery (CSB).

19. The method according to claim 18, wherein the cognition is assessed using at least one of the 7 domains of cognition relevant for patients with schizophrenia as assessed in the MCCB.

20. The method according to claim 18, wherein the cognition is assessed using at least 4 of the 7 domains of cognition relevant for patients with schizophrenia as assessed in the MCCB.

21. The method according to claim 18, wherein the cognition is assessed using the MCCB overall composite score.

22. The method according to claim 18, wherein the cognition is assessed using at least one of the 7 domains of cognition relevant for patients with schizophrenia as assessed in the MCCB, wherein the domain is selected from the group consisting of the Trail Making Test (processing speed), Neuropsychological Assessment Battery, mazes subtest (reasoning and problem solving), and the Wechsler Memory Scale, spatial span subtest (working memory).

23. The according to claim 14, wherein the patient is 50 years of age or younger.

24. The method according to claim 14, wherein the patient is on co-medication with an antipsychotic.

* * * * *